(12) United States Patent
Hearn et al.

(10) Patent No.: US 10,065,792 B2
(45) Date of Patent: Sep. 4, 2018

(54) PRESSURISED REFILL CANISTER WITH AN OUTLET VALVE

(71) Applicant: Kind Consumer Limited, London (GB)

(72) Inventors: Alex Hearn, London (GB); Ritika Gupta, London (GB); Rene Mauricio Gonzalez Campos, London (GB); Khine Zaw Nyein, Middlesex (GB)

(73) Assignee: KIND CONSUMER LIMITED, London (GB)

( * ) Notice: Subject to any disclaimer, the term of this patent is extended or adjusted under 35 U.S.C. 154(b) by 162 days.

(21) Appl. No.: 14/777,905

(22) PCT Filed: Mar. 25, 2014

(86) PCT No.: PCT/GB2014/050938
§ 371 (c)(1),
(2) Date: Sep. 17, 2015

(87) PCT Pub. No.: WO2014/155092
PCT Pub. Date: Oct. 2, 2014

(65) Prior Publication Data
US 2016/0280450 A1    Sep. 29, 2016

(30) Foreign Application Priority Data
Mar. 26, 2013 (GB) .................................. 1305486.1

(51) Int. Cl.
*B65D 83/14* (2006.01)
*A61M 15/00* (2006.01)
(Continued)

(52) U.S. Cl.
CPC ............ *B65D 83/752* (2013.01); *A24B 15/16* (2013.01); *A24F 47/002* (2013.01);
(Continued)

(58) Field of Classification Search
CPC ...... B65D 83/752; B65D 83/42; B65D 83/48; A61M 15/0093; A61M 15/06;
(Continued)

(56) References Cited

U.S. PATENT DOCUMENTS 3,277,674 A    10/1966 Klein et al.
2005/0193744 A1    9/2005 Cockings et al.
(Continued)

FOREIGN PATENT DOCUMENTS

FR    1244074 A    10/1960
GB    938331 A    10/1963
(Continued)

OTHER PUBLICATIONS

International Search Report and Written Opinion dated Jun. 25, 2014 for Application No. PCT/GB2014/050938.
(Continued)

*Primary Examiner* — Timothy L Maust
*Assistant Examiner* — Timothy P Kelly
(74) *Attorney, Agent, or Firm* — Patterson & Sheridan, LLP

(57) ABSTRACT

A pressurized refill canister containing a reservoir of composition including a propellant and a nicotine or a pharmaceutically acceptable derivative or salt thereof. The reservoir is at a pressure of greater than 400 kPa at 20° C. A refill outlet valve comprises a stem with an axial bore open at the axial end furthest from the reservoir to provide an outlet which discharges the composition in an axial direction. The stem is displaceable from a closed position to which it is biased by a first resilient member with a spring force of greater than 10N when no external force is applied to a dispensing position against the action of the first resilient member to open a flow path from the reservoir to the outlet.

24 Claims, 7 Drawing Sheets

(51) Int. Cl.
*A61M 15/06* (2006.01)
*B65D 83/42* (2006.01)
*B65D 83/48* (2006.01)
*A24F 47/00* (2006.01)
*A24B 15/16* (2006.01)
*A61M 16/20* (2006.01)

(52) U.S. Cl.
CPC ....... *A24F 47/006* (2013.01); *A61M 15/0091* (2013.01); *A61M 15/06* (2013.01); *A61M 16/20* (2013.01); *B65D 83/42* (2013.01); *B65D 83/425* (2013.01); *B65D 83/48* (2013.01); *A61M 2202/0468* (2013.01); *A61M 2209/045* (2013.01)

(58) Field of Classification Search
CPC ..... A61M 2202/0468; A61M 2209/045; A24F 47/002; A24F 47/006
See application file for complete search history.

(56) References Cited

U.S. PATENT DOCUMENTS

| | | | | |
|---|---|---|---|---|
| 2010/0229881 A1* | 9/2010 | Hearn | ................... | A24F 47/002 131/273 |
| 2010/0236562 A1* | 9/2010 | Hearn | ................... | A61K 9/0043 131/330 |
| 2016/0037826 A1* | 2/2016 | Hearn | ................... | A24F 47/002 141/3 |
| 2016/0052700 A1* | 2/2016 | Hearn | ................... | B65D 83/42 141/5 |

FOREIGN PATENT DOCUMENTS

| | | |
|---|---|---|
| GB | 1084253 A | 9/1967 |
| GB | 2198707 A | 6/1988 |
| GB | 2340477 A | 2/2000 |
| WO | 2008071901 A1 | 6/2008 |
| WO | 2009001078 A2 | 12/2008 |
| WO | 2009001085 A2 | 12/2008 |
| WO | 2010073018 A1 | 7/2010 |
| WO | 2011015825 A1 | 2/2011 |
| WO | 2011015826 A1 | 2/2011 |
| WO | 2011095781 A1 | 8/2011 |
| WO | 2011117580 A2 | 9/2011 |
| WO | 2014033437 A2 | 3/2014 |

OTHER PUBLICATIONS

United Kingdom Search Report dated Sep. 10, 2013 for Application No. GB1305486.1.

\* cited by examiner

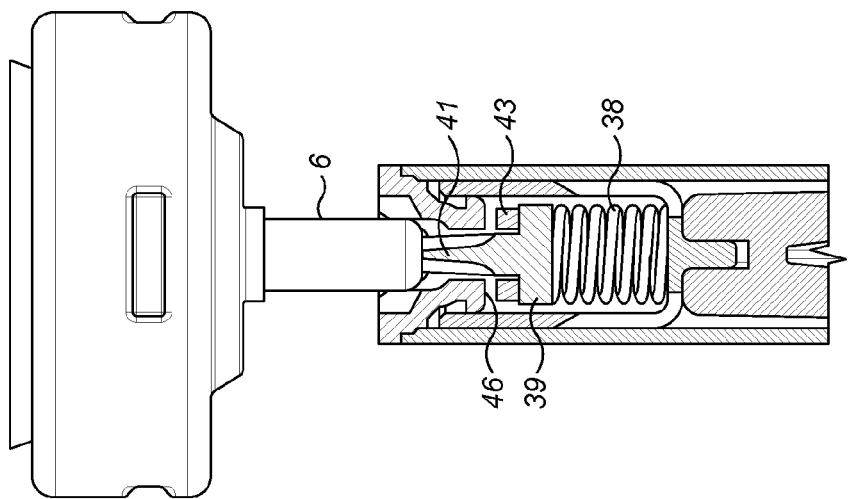
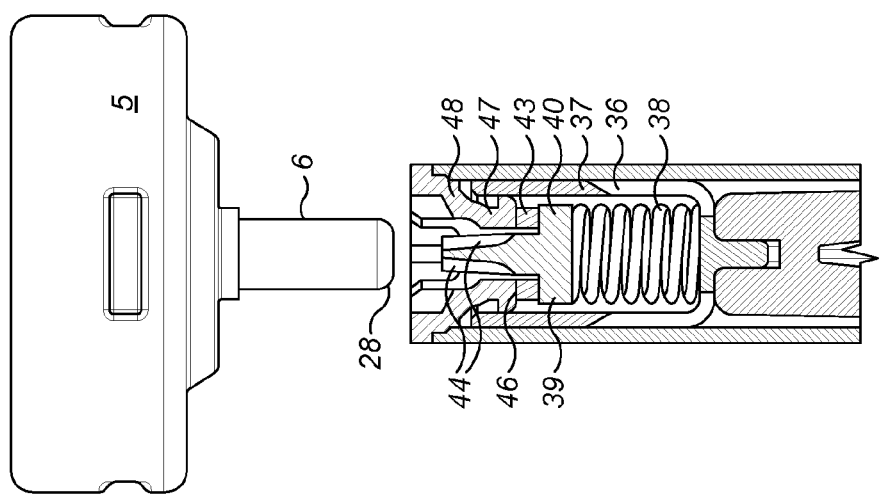
FIG. 5B
FIG. 5A

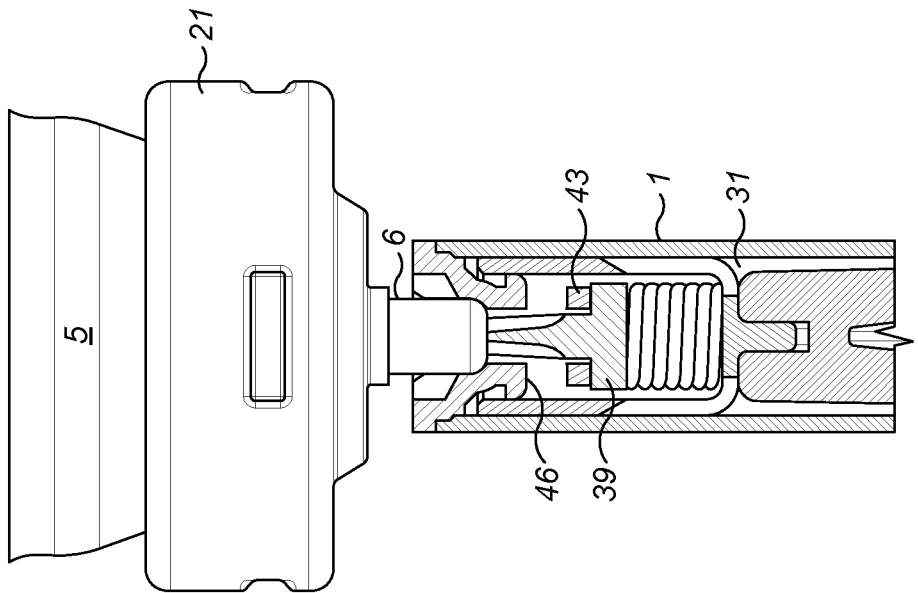
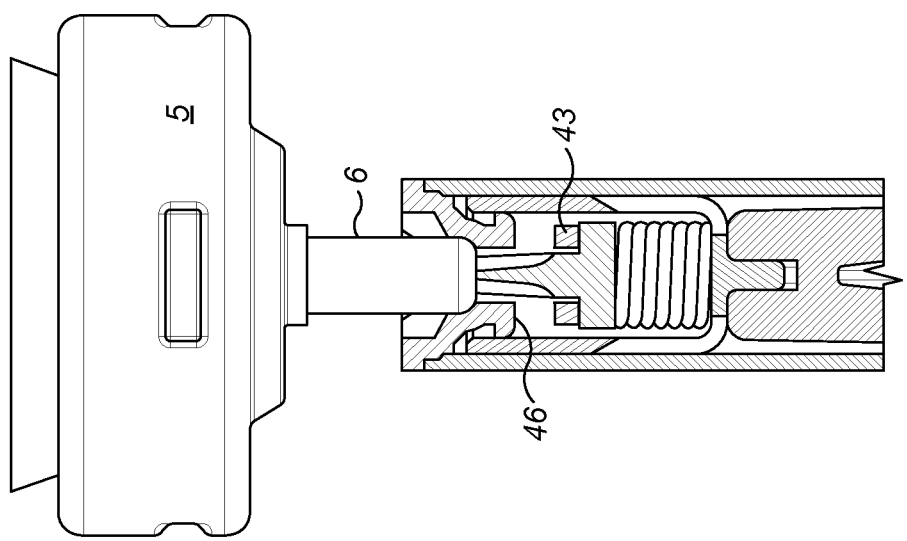
FIG. 5D
FIG. 5C

PRESSURISED REFILL CANISTER WITH AN OUTLET VALVE

The present invention relates to a pressurised refill canister with an outlet valve. It has been designed, in particular, for a refill for a simulated cigarette such as that disclosed in WO 2009/001078. However, it can also be used in other products which require a pressurised gas refill.

In WO 2009/001078, a simulated cigarette is proposed which has dimensions similar to those of a conventional cigarette. The cigarette has a reservoir to receive a pressurised gas including a propellant. The reservoir has a breath activated valve at one end (as described in greater detail in WO 2011/015825, WO 2011/015826) and a refill valve at the opposite end.

A refill pack which has the shape and size of a normal cigarette pack is provided with a cylinder of refill gas and has a fill valve which is arranged to mate with the refill valve in the cigarette to periodically refill the cigarette.

As described in WO 2009/001078, the device refill valve is a check valve which is biased into a closed position and the canister refill valve comprises a hollow nozzle with lateral ports and which is also spring-loaded. When the two are pushed together, the nozzle pushes the check valve away from its seat thereby initially venting the device. Subsequent pushing of the device onto the nozzle causes a shoulder on the refill to engage and mate with an annular seat on the end of the device in order to provide a seal. Subsequent movement causes the nozzle of the canister fill valve to be depressed against its spring thereby opening a flow path from the refill into the cigarette. The nozzle on the canister fill valve is provided with a pair of lateral outlets which are generally perpendicular to the central bore through the nozzle. The device valve seat, however, has a flat surface against which the cylindrical refill nozzle is pushed. Additionally, the refill nozzle has a considerably smaller diameter and higher length than the device refill valve inlet passage. This would result in a significantly high probability of misalignment during filling due to slippage thus providing a filling mechanism prone to damaging the refill nozzle.

Also relevant to the invention are refill valves used for butane gas to refill cigarette lighters and the like. Lighters are filled with butane, the expandability of which is significantly different from that of the propellant based system with which the present invention is concerned. It is also of a significantly lower pressure than the pressure required to refill a propellant based simulated cigarette. With a propellant based system, the propellant (such as hydrofluoroalkane (HFA)) will expand as liquid leaves the reservoir thereby maintaining a constant high pressure within the reservoir. With a butane based system, as the butane gas is depleted, the pressure in the reservoir drops. This means that they can be filled from a refill without necessarily needing to vent the chamber. This refill process for a butane system is typically assisted by the use of a relatively large cylinder which is held in an inverted configuration above the lighter in order to provide a gravity assist to the refill.

The connectivity between the lighter inlet valves and the outlet valve of a refill cylinder operate in a manner that allows it to perform the function of filling a reservoir without venting it. If the lighter reservoir gets filled with air due to an incorrect filling technique, the reservoir would need to be vented before filling. In this case, the venting procedure is the actuation of the refill valve using a device such as a pen or a screw driver to open the valve and allow any trapped air to escape. U.S. Pat. No. 3,277,674 discloses a refillable lighter with a vent path built into the valve of the lighter. There is no disclosure of the nature of the refill valve.

Also of some superficial similarity to the present invention are certain pressurised metered dose inhaler (PMDI) valves such as that described in WO2008/071901. These have a nozzle in the form of a blind bore which is closed at an innermost end and open at the opposite end with axially spaced lateral bores extending through the wall of the nozzle into the axial bore. The body of the dispenser is provided with annular seals which surround the nozzle such that, as the nozzle is depressed into the dispenser, the inner lateral bore passes the inner seal thereby placing the nozzle in communication with formulation in the canister and aiding in supply of formulation to the metering chamber. On further depression of the bore into the dispenser, the inner lateral bore passes further beyond the inner seal and a divider of the bore comes in line with the inner seal resulting in blockage of formulation flow from the dispenser into the metering chamber through the inner bore. At the same time, the outer lateral bore crosses the outer seal placing the outer bore in communication with formulation in the metering chamber. This results in flow of a metered quantity of formulation out of the chamber through the bore. In its unstressed configuration, the nozzle is biased into an outermost position by a spring in which the outer lateral bore is outside of the seal.

Such valves are not refill valves. Also, they are unsuitable for use in refilling a simulated cigarette as the metering chamber is much smaller than the cigarette. Refilling would therefore require the cigarette to be pressed against the valve multiple times, which would not work in practice, given the need to vent the cigarette prior to filling.

None of these documents is able to overcome the problems of WO2008/001078 and there is therefore nothing in the art which represents the robust and reliable valve for refilling a simulated cigarette at the relatively high pressures that it requires.

According to a first aspect of the present invention, there is provided a pressurised refill canister containing a reservoir of composition including a propellant and a nicotine or a pharmaceutically acceptable derivative or salt thereof, the reservoir being at a pressure of greater than 400 kPa at 20° C., and a refill outlet valve comprising a stem with an axial bore open at the axial end furthest from the reservoir to provide an outlet which discharges the composition in an axial direction, the stem being displaceable from a closed position to which it is biased by a first resilient member with a spring force of greater than 10N when no external force is applied to a dispensing position against the action of the first resilient member to open a flow path from the reservoir to the outlet.

The present invention therefore provides a relatively high pressure canister and axial outlet at the end of the bore, the stem being displaceable against a relatively high spring force. Such a device is readily suited to being pressed firmly against the fill valve of a simulated cigarette. Further, the fact that the refill valve is required to open against a high spring force means that it is reliably able to open the fill valve in a device to be refilled prior to opening of the fill valve in the canister. WO2009/001078 is not well suited to cope with the high spring force as the design of the nozzle means that there is a high probability of misalignment which limits the force that can be applied to open the reservoir. The greater the opening force that is required, the greater the force on the stem, and therefore the higher the probability that a misaligned valve element will prevent the fill valve from being opened correctly.

The composition preferably comprises a solvent which may be a monohydric alcohol and may further comprise a glycol and/or glycol ether. In this case, the ratio of monohydric alcohol:glycol or glycol ether by weight is from 6:1 to 1:1. Preferably, the composition comprises from 0.1 to 2% w/w proprolene glycol, based on the total weight of the composition. Preferably, the composition comprises from 0.5 to 1.5% w/w ethanol based on the total weight of the composition.

The propellant is preferably a hydrofluorocarbon.

Preferably, the composition further comprises from 0.001% w/w to 0.45% w/w and more preferably 0.026% w/w to 0.084% w/w nicotine or pharmaceutically acceptable derivative or salt thereof, based on the total weight of the composition.

Further details and advantages of the composition are provided in our earlier filed application GB 1215273.2.

The outer diameter of the stem is preferably greater than 3 mm.

The refill valve may be a metered valve, provided that it has a relatively large metering chamber. However, preferably, it is a non-metered valve.

Preferably the stem is closed at the end opposite the outlet to create a blind bore and further comprises a lateral bore in the side wall of the stem leading to the blind bore, the refill outlet valve further comprising an annular seal which surrounds the stem whereby, in the first position, the lateral bore is not in communication with the inside of the canister, and in the dispensing position, the lateral bore is arranged to move inside the canister with respect to the seal to open a flow path from the inside of the canister via the lateral bore and along the blind bore to the outlet end.

A refill valve with a lateral bore which moves in against the resilient member into selective communication with the canister through a seal provides a simple robust mechanism for achieving a non-metered refill outlet.

Preferably in the first position, the annular seal covers and seals the lateral bore.

If the lateral bore were to be positioned as it is for a PMDI valve as mentioned above, this would provide an unintended vent path via the valve stem which is open to allow the composition to escape during disengagement. By covering the lateral bore with the seal, there is no such vent path as the lateral bore does not travel out beyond the seal.

Preferably, the radially outermost edge of the stem at the outlet end is rounded. This rounded edge provides an improved seal with a device to be refilled even in the event of a slight misalignment between the stem and the device.

A further potential problem faced by a refillable device which is designed to contain an inhalable composition is the potential for the reservoir to be filled with an unauthorised substance. For example, if the device could be refilled from a butane gas refill, this could be dangerous for the user.

Therefore, preferably the stem has a maximum outer diameter of greater than 3 mm and, wherein, at the outlet end of the stem, at least part of the wall of the stem extends inwardly from the outside diameter for at least 50% of the radius.

This may be expressed in slightly different terms as the stem having a maximum outer diameter of greater than 3 mm and, wherein, within a circle defined at the outlet end having a diameter of 1.5 mm, there is a feature present.

In general, for butane gas refills and the like, the stem has a relatively small outer diameter and a relatively thin wall in order to maximise the bore size and hence the flow rate for a given size of stem.

By providing a significantly larger outer diameter which also extends inwardly to a significant extent for at least part of its circumference. It may have a relatively thick wall. A similar effect may be achieved with an annular end cap which has the required dimensions. Alternatively, the stem has a localised feature, such as a single spoke or a cruciform extending across the bore, or a pin which is supported in the stem and occupies a central portion of the stem at its outlet end. For the purpose of this invention, the pin, in this case, is considered to be an extension of the wall.

In such an arrangement, the device can be dimensioned such that it will only work with a stem which fulfils these requirements. A stem such as the conventional butane stem which has an outer diameter which is too small will be unable to seal against the seat such that significant quantities of the composition will leak around the stem during the refill process rendering it useless as a refill device in practice. Secondly, any refill with a larger outer diameter, but which has a conventional thin wall will be able to engage with the seat in the device, but will not be able to press against the fill valve element as there is nothing at the centre of such a stem which is in a position to press against the fill valve element. By having a thicker wall, the stem according to the fourth and fifth aspects of the invention is able to press against the fill valve element so that it correctly operates the device.

As far as we are aware, there are no refill canisters, at present, that have a stem which has the above requirements. There is therefore no possibility that the device could be refilled with a hazardous substance from any known refill canisters.

According to a second aspect of the present invention, there is provided a combination of a pressurised refill canister according to the previous aspects of the present invention in combination with a device to be refilled, the device comprising a reservoir with a fill valve and an outlet valve, the fill valve comprising a seat to receive the outlet end of the stem, a valve element projecting into the seat and being biased by a second resilient member having a spring force which is less than the spring force of the first resilient member into a position in which it closes the fill valve, the valve element projecting into the seat to such an extent that, when the stem is inserted into the seat, it displaces the fill valve element to open a vent flow path around the valve element and around the outside of the stem, the stem being arranged such that further pressure urging the device and canister together causes the stem to land in the seat and the refill outlet valve to open, thereby creating a flow path from the canister into the device reservoir.

This combination provides for a very simple refill operation as far as a user is concerned. They simply need to press the device against the stem in the refill canister with a smooth action. The device will then automatically vent as the fill valve element is displaced, whereupon the increasing pressure applied by the user will open the refill outlet valve and refill the container. The user should hear and possibly see a spray of formulation venting. This then stops when the refill outlet valve is open. Further to this, the user would feel a slight push back when the device reservoir is full.

The device is preferably a simulated cigarette.

Preferably, the device outlet valve is a breath activated valve and/or the composition contains nicotine.

A portion of the seat facing the stem preferably has a generally part spherical surface which is complimentary with a rounded outermost edge of the stem. This means that, even if the stem is slightly misaligned with respect to the valve seat, the rounded surface of the seat and the rounded edge of the stem will still make reliable contact thereby reducing the potential for any leakage between the stem and the seat during the refill process.

In order to further facilitate the alignment of the stem with respect to the seat, both the stem and the seat have parallel sided portions which are complementary to one another. These parallel sided portions serve to guide the stem into the seat. Preferably, however, the length of the overlap of the parallel sided portions when fully mated with one another extends for less than 8 mm and more preferably less than 3 mm.

According to a third aspect of the present invention, there is provided a method of using a combination according to the sixth aspect of the present invention to refill the device, the method comprising the steps of pressing the device against the stem of the outlet valve with a first force to open the device fill valve against action of the second resilient member to vent the device reservoir via a path between the stem and the seat; and increasing the force with which the device seat is pressed against the stem to overcome the force of the first resilient member to open a flow path from the refill canister into the device reservoir and disengaging the device from the stem to close the refill outlet valve and device fill valve.

An example of a refill canister, a combination of canister and refillable device and method in accordance with the various aspects of the present invention will now be described with reference to the accompanying drawings, in which:

FIGS. 5A-5D are cross-sections showing the fill valve in the simulated cigarette together with a side view of the refill valve is disengaged, venting, landed and fill positions respectively;

Figure 1:
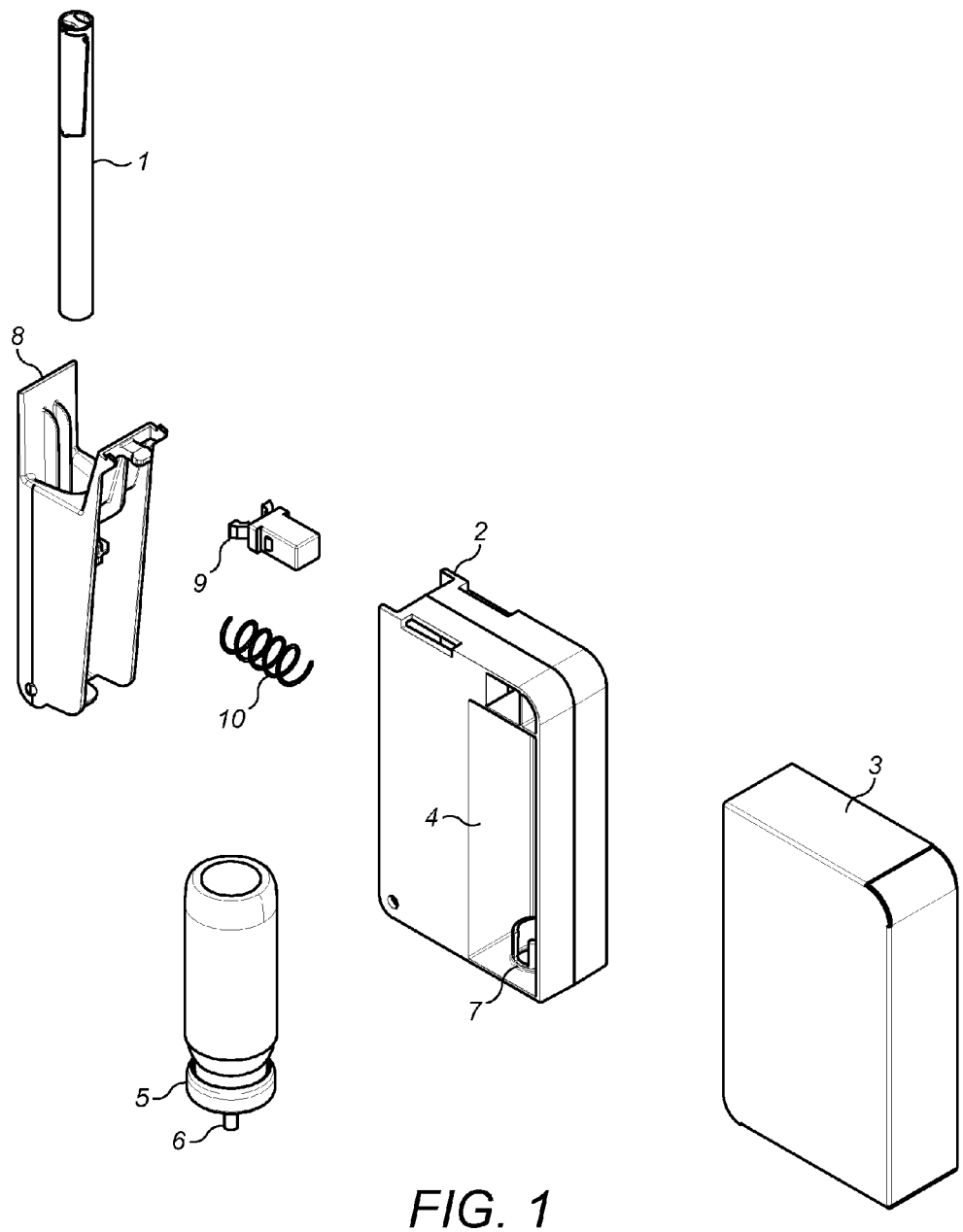
FIG. 1 is an exploded perspective view showing the refill canister and a simulated cigarette as well as the packaging.
Figure 2:
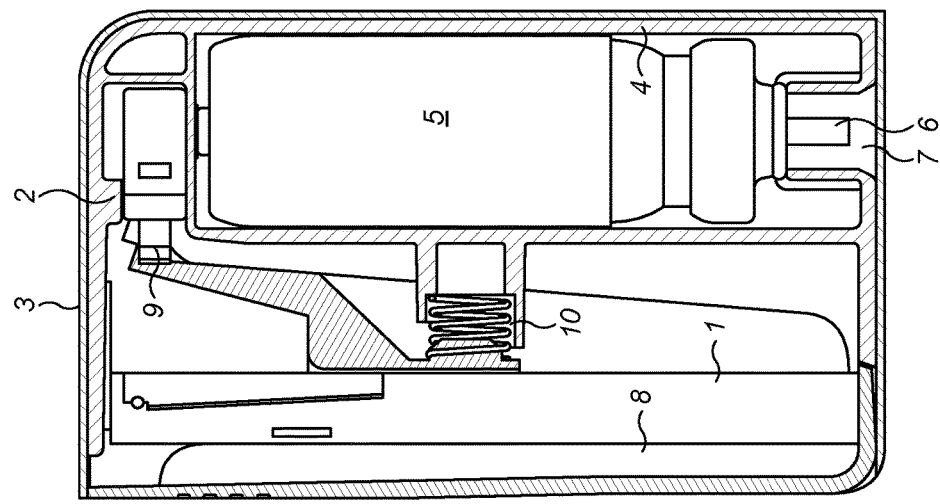
FIG. 2 is a cross-sectional view of the arrangement shown in FIG. 1 in a position in which a user can withdraw the simulated cigarette from the housing.
Figure 3:
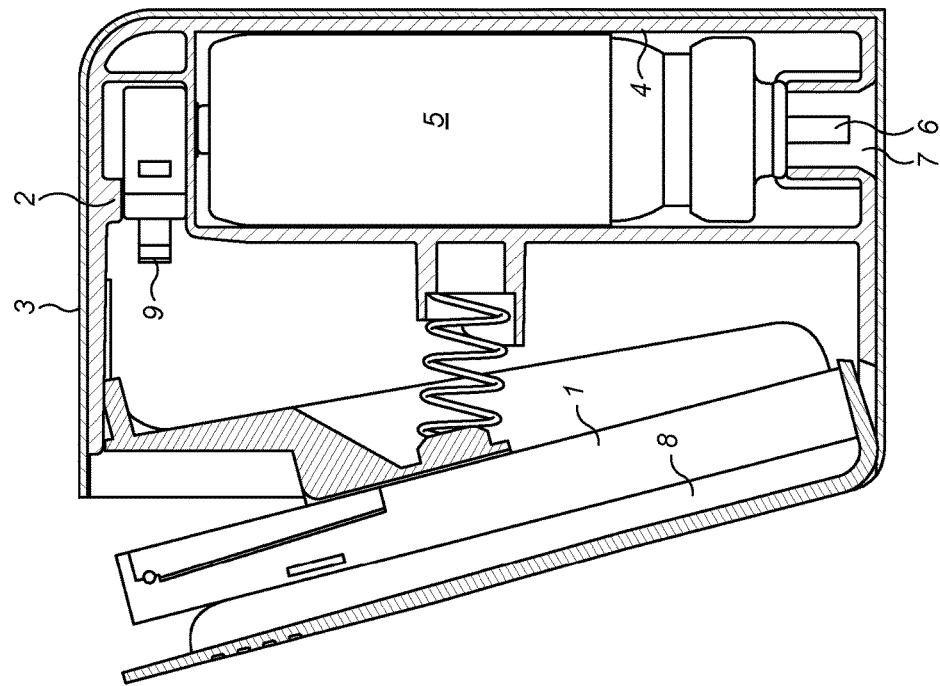
FIG. 3 is a view similar to FIG. 2 showing the cigarette in a storage position.

The simulated smoking device comprises a simulated cigarette 1 which, other than its refill valve, is as described in WO 2009/001078. This has a reservoir for an inhalable composition, a breath operated valve and a refill valve described below. Other than the refill valve, the cigarette will not be described further here. Further modifications to the simulated cigarette device are disclosed in our own earlier applications WO 2010/073018, WO 2011/015825, WO 2011/015826 and WO 2011/117580.

The composition of the reservoir is described in WO 2009/001085. Further details are provided in WO 2014/033437.

The remainder of the simulated smoking device is the refill device. This comprises a main housing portion 2 which is a plastics moulding. This is surrounded by a thin card sleeve 3 on which is printed various information such as promotional information. The size of the housing is preferably similar to the size of a cigarette pack and may be adjusted to suit particular sizing formats, e.g., to be the size of pack of 10 or 20 cigarettes. The housing 2 has a recess 4 in which is contained refill canister 5 of pressurised refill gas. The canister 5 has an outlet stem 6 at its lowermost end. With the canister 5 in the recess 4, the nozzle 6 sits above refill outlet orifice 7. The simulated cigarette device 1 is refilled by being pressed against the refill outlet orifice 7 as described in detail below. The canister may instead simply be a stand alone cylinder which could then have a larger capacity as it is not constrained by needing to fit within a cigarette pack sized housing.

In general terms, the housing 2 is divided into two halves with one half containing the refill gas canister 5 and the other part containing a hinged drawer 8 with a release mechanism 8 biased by a spring 10. This arrangement forms the subject of WO 2011/095781.

Figure 6A:
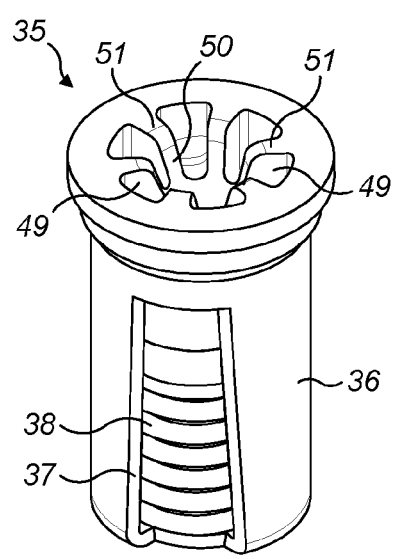
FIG. 6A is a perspective view of the fill valve.
Figure 6B:
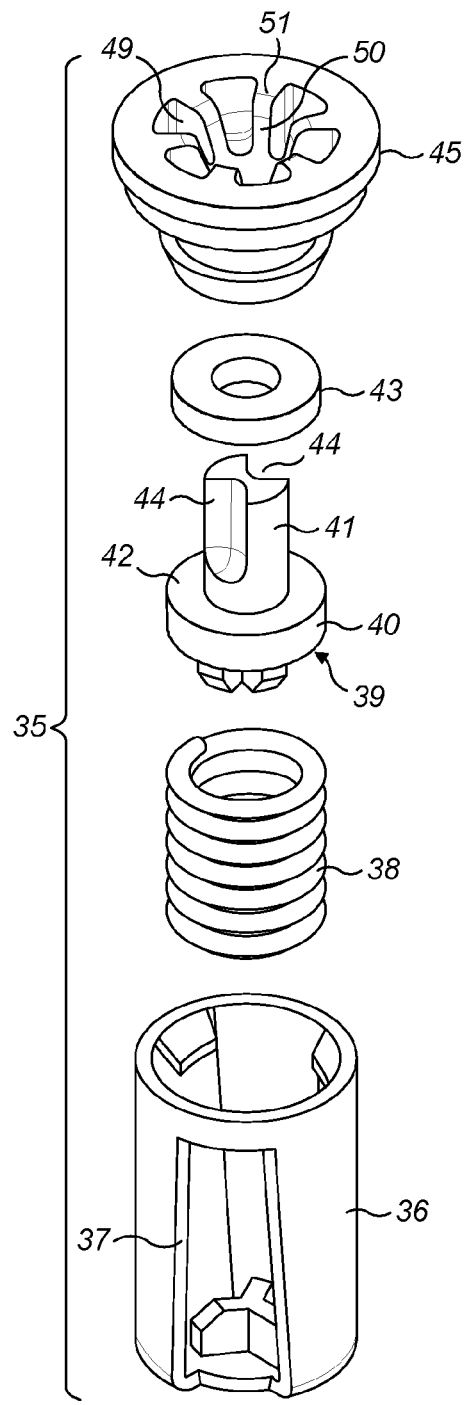
FIG. 6B is an exploded view of FIG. 6A.

This disclosure relates to improvements to the design of the refill valve of the refill canister 5 as will be described below with reference to FIG. 4 and/or the fill valve of the simulated cigarette 1 described below with reference to FIGS. 6A and 6B. The interaction between the two in the refill operation is illustrated in FIGS. 5A-5D.

The refill valve 20 of the refill canister 5 is a non-metered valve which is modified from the valve of a pressurised metered dose inhaler. FIG. 4 shows the end cap 21 of the refill canister 5 which has an annular configuration and surrounds the valve. Within the cap is an outer annular seal 22 and an inner annular seal 23 which, in the PMDI valve design form the ends of a metering chamber.

Figure 4:
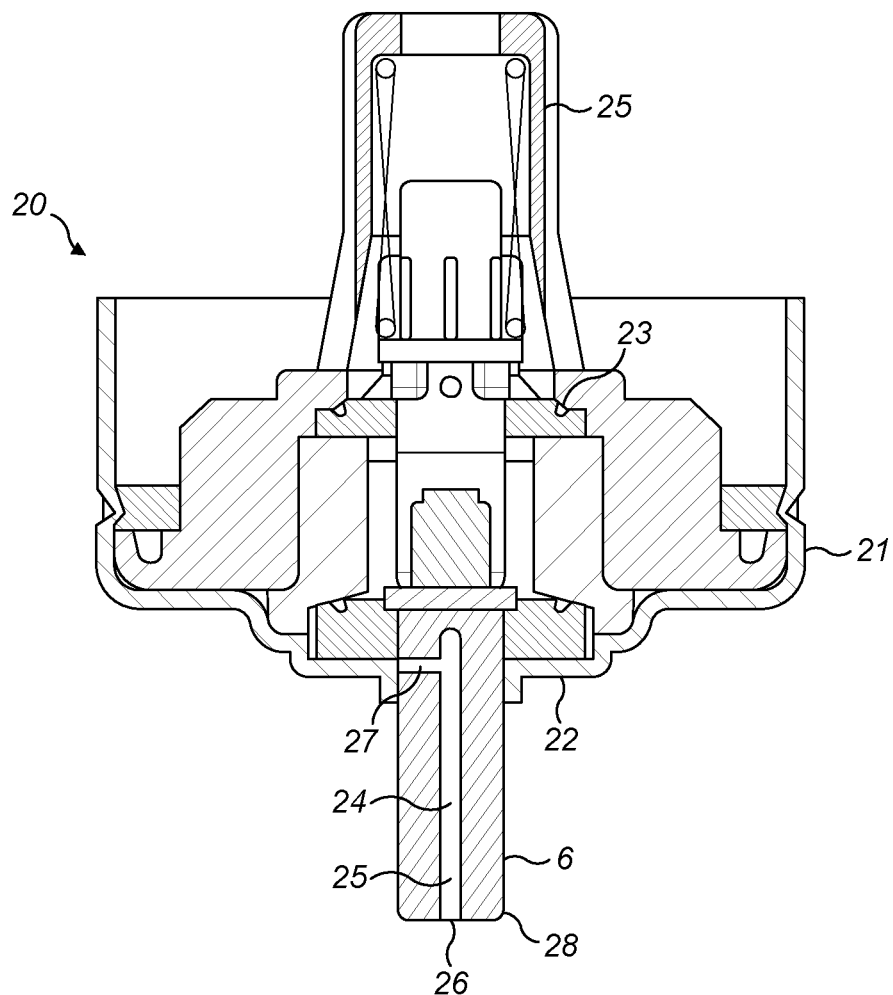
FIG. 4 is a cross-sectional view through the refill valve.

The valve stem 6 is slidable within the seals 22, 23 against the action of a spring 25 which provides a biasing force of greater than 5N and preferably greater than 10N in the at rest position shown in FIG. 4. The valve stem 6 is provided at its outlet end with an axial bore 24 which extend axially inwards from an outlet 26. A lateral bore 27 extends radially outwardly from the axial bore 24 to the outer periphery of the stem 6. In the at rest position shown in FIG. 4, lateral bore 27 is covered by the outer annular seal 22. The seal between the outer seal 22 and the outer periphery of the valve stem 26 prevents flow out of the refill canister.

In the metered valve on which this design is based, the valve stem is further provided with an outer periphery which seals with the inner annular seal 23 with a bore through the stem which provides selective communication with the metering chamber between the annular seals in order to charge the chamber. In the present case, however, the stem 6 has a non-circular cross-section in the vicinity of the inner annular seal 23 such that it does not seal with the inner annular seal and the chamber between the two annular seals 22, 23 is always open to the main reservoir within the refill canister 5. This renders the valve a non-metered valve.

The refill canister 5 is designed to operate in the inverted configuration as shown in FIGS. 1 to 4. It could, however, alternatively operate the opposite way up if a dip tube were provided to communicate between the bottom portion of the canister and the refill valve 20.

When the outlet stem 6 is depressed, once the lateral bore 27 passes the outer seal 22, this opens a flow path from the inside of the refill canister through the lateral bore 27 and along the axial bore 24 to the outlet 26.

As shown in FIG. 4, the radially outermost edge of the outlet end of the outlet stem 6 has a curved profile 28 for the reasons described below.

The fill valve 35 in the cigarette 1 will be described with reference to FIGS. 6A and 6B.

The cigarette 1 has an inhaling end 30 associated with a breath activated valve (not shown), such that sucking on the inhaling end 30 opens the breath activated valve allowing a user to inhale the contents of the reservoir 31. At the opposite end to the inhaling end 30 is the fill end 32 which is provided with the fill valve 35 as shown in FIGS. 6A and 6B.

The fill valve comprises a cage 36 which supports the remaining valve components within the fill end 32 of the reservoir 31. The cage has a number of large lateral openings 37 which allow open communication between the inside of the cage 37 and the remainder of the reservoir 31.

Contained within the cage is a second spring 38 which biases a valve element 39 into a closed position as shown in FIG. 5A. The valve element 39 has a circular base 40 from the centre of which of which a spigot 41 projects upwardly. The lower surface of the base 40 is arranged to receive the top of the spring 38, while the upper annular surface 42 receives an annular sealing element 43 which surrounds the lower part of the spigot 41. As best seen in FIG. 5A, the spigot 41 has a number of axially extending flow channels 44 which begin above the annular sealing element 43 and extend to the uppermost surface of the spigot 41.

The fill valve 35 is completed by end cap 45 which has a lowermost annular surface 46 which seals with the upper face of the annular sealing element 43. The end cap has a central opening 47 through which the spigot 41 projects. The central opening 47 opens out into a generally part spherical seat 48 which further opens out into a castellated region which comprises a number of radially inwardly extending projections 49, the inner faces 50 of which have a part cylindrical configuration to provide a guideway for the outlet stem 6 as described below. Each face 50 has a tapered lead in surface 51.

In order to refill the reservoir 31 of the cigarette 1, the fill end 32 of the cigarette 1 is presented to the outlet stem 6 of the refill canister 5 as shown in FIG. 5A. At this time, the fill valve 35 of the reservoir 31 is closed as the spring 38 urges the valve element 39 into its uppermost position in which the annular sealing element 43 seals against the lowermost annular surface 46 on the end cap 45. Similarly, the refill outlet valve 20 is closed as the lateral bore 27 is sealed by the outer annular seal 22.

As the cigarette 1 is pressed into the stem 6, initially, the flared lead-in surfaces 51 of the projections 49 in cooperation with the curved profile 28 on the outlet stem 6 assist the user in lining the cigarette 1 with the stem 6. Subsequently, the cylindrical face of the stem 6 engages with the inner faces 50 of the projections 49 thereby ensuring that the cigarette 1 is in general axial alignment with the stem 6. Any slight misalignment between the cigarette 1 and the stem 6 is accommodated, to some extent, by the generally spherical nature of the seat 48 in the end cap 45 and the curved profile 28 on the end of the stem 6 as described below.

As shown in FIG. 5B, as soon as the stem 6 engages with the uppermost surface of the spigot 41 of the valve element 39, it begins to move the valve element 39 downwardly. This is because the second spring 38 exerts a weaker force than the first spring 25 so that the valve element 39 begins to move before the stem 6 is displaced. This moves the annular sealing element 43 away from the lowermost annular surface 46 thus opening a vent flow path from the reservoir, around the base 40 of the valve element 39, between the annular sealing element 43 and the lowermost surface 46 of the end cap 45, along the flow channels 44 and out of the cigarette 1.

Once the cigarette 1 is engaged to the extent that the curved profile 28 lands in the seat 48 as shown in FIG. 5C, the next phase of opening begins. In this position, the cigarette can continue to vent as the seat 48 does not form a perfect seal with the curved profile 28 at the end of the stem 6. As the valve element 39 cannot be depressed further, application of additional pressure to the cigarette 1 will now cause the stem 6 to be pushed upwardly into the refill canister 5 against the action of the first spring 25 until the lateral bore 27 is moved inwardly of the outer annular seal 22. This opens a refill flow path from the refill canister 5 along lateral bore 27 and axial bore 24, through outlet 26, along flow channels 44 and into the reservoir 31 via the space between the annular sealing element 43 and the lowermost annular surface 46 of the end cap 45. During this period, little or no flow passes through the interface between the seat 48 and the end of the stem 6 as, although, as mentioned above, this surface is not sealed, the above mentioned refill flow path provides a much larger and more direct flow path for the composition from the reservoir such that any leakage around the valve stem is kept to a minimum. Further, the spherical nature of the seat 48 and curved profile 28 at the tip of the stem 6 ensures that this leakage is kept to a minimum even if the cigarette 1 is angularly off-set to a small degree from the axis of the stem 6. Larger angular off-sets are generally prevented by the projections 49 engaging with the stem.

When the reservoir 31 is full of composition, the user will feel a slight push-back as the pressure in the reservoir 31 equalises with the pressure in refill canister 5 thereby preventing further flow. They then pull the cigarette 1 away from the canister 5 which quickly causes the two springs 25, 38 to return their respective valves to the closed position.

The arrangement at the end of the outlet stem 6 will now be described with reference to FIGS. 7 and 8.

The dimensions required at the end of the outlet stem are best illustrated defined with reference to the prior art. A nozzle of the kind used for a butane gas refill, has a relatively small external diameter and a thin wall. The approach taken in the present case is to have a much larger external diameter and a relatively thick wall, or at least some other feature present towards the central region at the end of the nozzle. The reason for this is apparent, for example, from FIG. 5B. A relatively large outer diameter is required in order to reliably engage with the seat region 48. The presence of a thick wall or some other feature towards the central region of the end is necessary in order to bear against the top of the spigot 41 to depress the valve element 39. If a conventional butane gas refill is used to try to fill the cigarette, its relatively thin nozzle would not contact the seat 48 and would therefore provide a leak path around the stem. This would render it useless in practice. Also, if a stem with a larger outer diameter, but a conventional wall thickness were to be used, this would be able to engage the seat 48 adequately. However, the open space at the centre of the stem would be so large that it would simply fit over the spigot 41 and would not be able to depress it.

Figure 7:
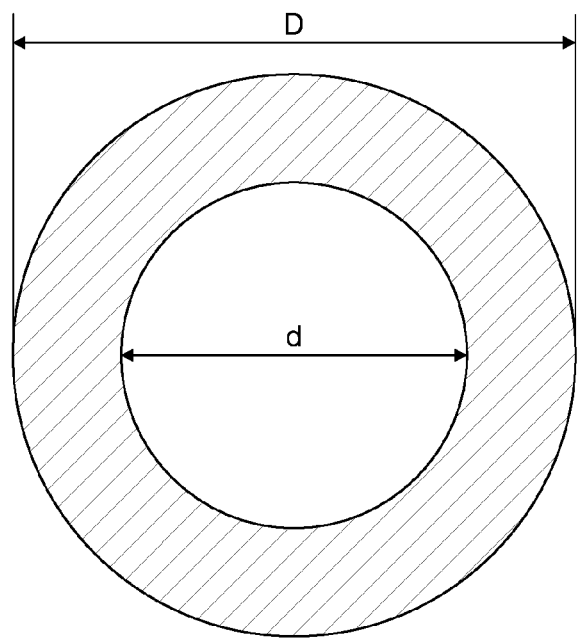
FIG. 7 is a diagram explaining the end dimensions of the outlet stem.

The current outlet stem has an outer diameter D of at least 3 mm as shown in FIG. 7. For the purpose of calculating this diameter D, the curved profile 28 at the outlet end is disregarded. Within the circle of diameter D, a second concentric circle with a diameter of d of 1.5 mm is defined within which there must be something present at the end face of the nozzle. In other words, at the end of the nozzle, if there is an inner circular diameter d with a diameter of 1.5 mm which has no feature present, it will not be able to engage with the spigot 41.

The preferred dimensions for the nozzle 6 are an outer diameter of 3.15 mm to 3.20 mm, an inner diameter of 1.10 m to 1.30 mm.

Figure 8A:
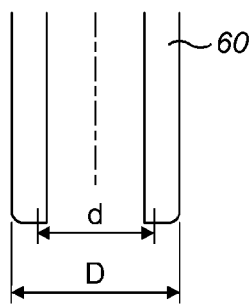
FIGS. 8A-8D are cross-section showing cross-sections showing various stem configurations.

FIG. 8A shows a nozzle with a relatively thick wall 60. The wall is of sufficient thickness that it extends inside the inner circle d.

Figure 8B:
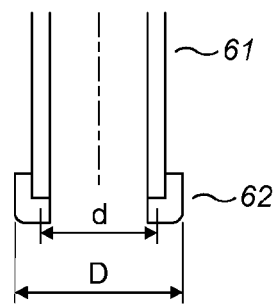

A similar effect is achieved in FIG. 8B which has a thin walled tube 61 with an end cap to provide the required dimensions.

Figure 8C:
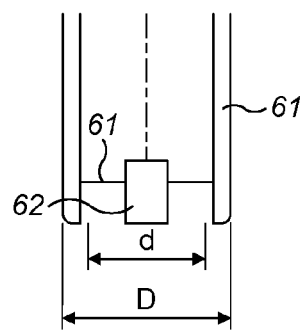

FIG. 8C has a similar thin wall, but has a pin 62 supported at the outlet end by spokes 61. As is apparent from FIG. 8C, the pin 62 is present within the inner circle d and would be able, in use, to engage with the spigot 41.

Figure 8D:
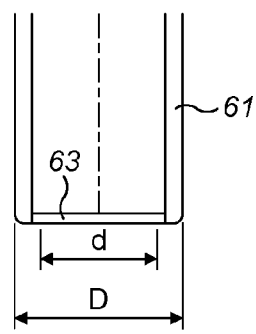

Finally, in FIG. 8D, a crossbar 63 extends diametrically across the end of the nozzle. This may alternatively be a cruciform or some other intermittent feature which is able to engage with the spigot 41.

The invention claimed is:

1. A pressurised refill canister containing a reservoir of composition including a propellant and a nicotine or a pharmaceutically acceptable derivative or salt thereof, the reservoir being at a pressure of greater than 400 kPa at 20° C., and a refill outlet valve comprising an elongated stem having an axial bore open at an axial end furthest from the reservoir to provide an outlet which discharges the composition in an axial direction, the stem being displaceable from a closed position to which it is biased by a first resilient member with a spring force of greater than 10N when no external force is applied to a dispensing position against the action of the first resilient member to open a flow path from the reservoir to the outlet, and wherein an outer diameter of the stem is greater than 3 mm.

2. A canister according to claim 1, wherein the composition further comprises a solvent.

3. A canister according to claim 2, wherein the solvent comprises a monohydric alcohol.

4. A canister according to claim 3, wherein the solvent further comprises a glycol and/or glycol ether.

5. A canister according to claim 4, wherein the ratio of monohydric alcohol:glycol or glycol ether by weight is from 6:1 to 1:1.

6. A canister according to claim 4, wherein the composition comprises from 0.1 to 2% w/w propylene glycol, based on the total weight of the composition.

7. A canister according to claim 6, wherein the composition comprises from 0.5 to 1.5% w/w ethanol, based on the total weight of the composition.

8. A canister according to claim 1, wherein the propellant is a hydrofluorocarbon.

9. A canister according to claim 1 wherein the composition comprises from 0.001% w/w to 0.45% w/w and preferably 0.026% w/w to 0.084% w/w nicotine or pharmaceutically acceptable derivative or salt thereof, based on the total weight of the composition.

10. A canister according to claim 1, wherein the refill outlet valve is a non-metered valve.

11. A canister according to claim 10, wherein the stem is closed at the end opposite the outlet to create a blind bore and further comprises a lateral bore in the side wall of the stem leading to the blind bore, the refill outlet valve further comprising an annular seal which surrounds the stem whereby, in the first position, the lateral bore is not in communication with the inside of the canister, and in the dispensing position, the lateral bore is arranged to move inside the canister with respect to the seal to open a flow path from the inside of the canister via the lateral bore and along the blind bore to the outlet end.

12. A canister according to claim 11, wherein in the first position, the annular seal covers and seals the lateral bore.

13. A canister according to claim 1, wherein the radially outermost edge of the stem at the outlet end is rounded.

14. A pressurised refill canister according to claim 1, wherein the stem has a maximum outer diameter of greater than 3 mm and, wherein, at the outlet end of the stem, at least part of the wall of the stem extends inwardly from the outside diameter for at least 50% of the radius.

15. A canister according to claim 14, wherein the wall of the stem at the outlet end has a thickness which extends for at least 50% of the radius.

16. A canister according to claim 14, wherein the stem has an annular end cap to define its dimensions at the outlet end.

17. A canister according to claim 14 wherein the stem has a localised feature at the outlet end.

18. A combination of a canister according to claim 1, and a device to be refilled, the device comprising a reservoir with a fill valve and an outlet valve, the fill valve comprising a seat to receive the outlet end of the stem, a valve element projecting into the seat and being biased by a second resilient member having a spring force which is less than the spring force of the first resilient member into a position in which it closes the fill valve, a fill valve element of the fill valve projecting into the seat to such an extent that, when the stem is inserted into the seat, it displaces the fill valve element to open a vent flow path around the fill valve element and around the outside of the stem, the stem being arranged such that further pressure urging the device and canister together causes the stem to land in the seat and the refill outlet valve to open, thereby creating a flow path from the canister into the device reservoir.

19. A combination according to claim 18, wherein a portion of the seat facing the stem has a generally part spherical surface which is complementary with the outermost edge of the stem.

20. A combination according to claim 18, wherein both the stem and the seat have parallel sided portions which are complementary to one another.

21. A combination according to claim 20, wherein the length of the overlap of the parallel sided portions when fully mated with one another extends for less than 8 mm.

22. A combination according to claim 18, wherein the pressure differential between the first and second resilient members in their unstressed state is 15N.

23. A combination according to claim 18, wherein the refill reservoir pressure, the dimensions of the flow path and the capacity of the reservoir of the device to be filled are such that, with the refill canister and device to be filled fully engaged, the device reservoir will fill in less than 10 seconds.

24. A method of using a combination according to claim 18 to refill the device, the method comprising the steps of pressing the device against the stem of the outlet valve with a first force to open the device fill valve against action of the second resilient member to vent the device reservoir via a path between the stem and the seat; and increasing the force with which the device seat is pressed against the stem to overcome the force of the first resilient member to open a flow path from the refill canister into the device reservoir and disengaging the device from the stem to close the refill outlet valve and device fill valve.

* * * * *